United States Patent [19]

Kurihara

[11] Patent Number: 5,395,921
[45] Date of Patent: Mar. 7, 1995

[54] CURCULIN C

[75] Inventor: Yoshie Kurihara, Tokyo, Japan

[73] Assignees: Yoshie Kurihara; Asahi Denka Kogyo Kabushiki Kaisha, both of Tokyo, Japan

[21] Appl. No.: 165,754

[22] Filed: Dec. 10, 1993

Related U.S. Application Data

[63] Continuation of Ser. No. 934,722, Aug. 24, 1992, abandoned.

[30] Foreign Application Priority Data

Oct. 1, 1991 [JP] Japan .................. 3-253914

[51] Int. Cl.⁶ .................. A61K 37/02; C07K 15/10
[52] U.S. Cl. .................. 530/350; 530/324
[58] Field of Search .................. 530/350, 324

[56] References Cited

U.S. PATENT DOCUMENTS

| 5,176,937 | 1/1993 | Kurihara et al. | 426/655 |
| 5,178,899 | 1/1993 | Kurihara et al. | 426/655 |
| 5,178,900 | 1/1993 | Kurihara et al. | 426/655 |
| 5,242,693 | 9/1993 | Kurihara et al. | 426/3 |

FOREIGN PATENT DOCUMENTS 2-104263 4/1990 Japan .
3-190899 8/1991 Japan .

OTHER PUBLICATIONS

Biotechnology Products Catalog, Pharmacia, pp. 50–52, 57 and 73, 1993.
Biochemicals Organic Compounds for Research and Diagnostic Reagents, Sigma Chem. Co., pp.1 595–1596, 1993.
Harris & Angal, "Protein Purification Methods," IRL Press, pp. 179–182, 203–207, 1989.

*Primary Examiner*—Michael G. Wityshyn
*Assistant Examiner*—C. Sayala
*Attorney, Agent, or Firm*—Frishauf, Holtz, Goodman & Woodward

[57] ABSTRACT

Curculin C of the present invention has an intrachain disulfide linkage formed between the 29th cysteine residue and the 52nd cysteine residue and interchain disulfide linkages formed between the 77th cysteine residues of two curculin C monomer chains and between the 109th cysteine residues of two curculin C monomer chains, thus giving a dimer, and the monomer has an amino acid sequence as specified in SEQ ID No: 1.

1 Claim, 11 Drawing Sheets

```
           5           10          15          20          25          30
         D-N-V-L-L-S-G-Q-T-L-H-A-D-H-S-L-Q-A-G-A-Y-T-L-T-I-Q-N-K-C-N-
         └──────── N ────────┴─────20─────────────────┘  The rest
                                                          is omitted
         └──────── LEP-3 ──────────────────────┘
                                              25
         └──────── CH-6 ────────┘  ┌─ CH-4A ──
                                 21 22
                    35          40          45          50          55          60
         L-V-K-Y-Q-N-G-R-Q-I-W-A-S-N-T-D-R-R-G-S-G-C-R-L-T-L-L-S-D-G-
 LEP-3 ──┘  └──────────────────── LEP-5 ────────────────────────
         33 34
 CH-4A ──┘  └─ CH-4B ─┘  └──────── CH-10 ────────────
         34 35        41 42
                                              └── T-11 ──
                                              54
                    65          70          75          80          85          90
         N-L-V-I-Y-D-H-N-N-N-D-V-N-G-S-A-C-W-G-D-N-G-K-Y-A-L-V-L-Q-K-
 ── LEP-5 ──┘                                      └─ LEP-2 ─┘
            67                                    83 84      90
 ── CH-10 ──┘                                     └── CH-13 ──
            66                                    84 85
 ──────── T-11 ────────────────────────┘
                                       87    90
                         95         100        105        110
         D-G-R-F-V-I-Y-G-P-V-L-W-S-L-G-P-N-G-C-R-R-V-N-G
         └──────── LEP-6 ──────────────────┘
         91                                112  114
         └── CH-13 ──┘  └── CH-H3 ──────────┘
                    102 103                 114
```

CURCULIN C

This application is a continuation of application Ser. No. 07/934,722, filed Aug. 24, 1992, (abandoned).

BACKGROUND OF THE INVENTION

1. Field of the Invention

This invention relates to curculin C (one of curculin homologue) having a stable and potent taste-modification effect, which is obtained from Curculigo latifolia.

2. Description of the Prior Art

The present inventors formerly found out a substance serving as a taste-modifier, which was named "curculin (curculin homologue, hereinafter referred to as curculin)" by them, from Curculigo latifolia fruits growing in Western Malaysia and the southern part of Thailand and belonging to the genus Curculigo of the family Hypoxidaceae or Amaryllidaceae. Further, they found out that this curculin was a protein and that a sour material or water taken after eating it would taste sweet, and applied for a patent based on these findings (refer to Japanese- Patent Laid-Open No. 104263/1990.) Subsequently, they succeeded in highly purifying this protein curculin (one of curculin homologue, hereinafter referred to as curculin A) and applied for a patent on a taste-modifier having the amino acid sequence thereof (refer to Japanese Patent Laid-Open No. 190899/1991).

In spite of the accomplishment of these inventions, however, it has been desired to develop a substance having a more stable and potent taste-modification activity.

SUMMARY OF THE INVENTION

It is an object of the present invention to provide curculin C having a stable and potent taste-modification activity which has a novel amino acid sequence and occurs as a dimer.

In the curculin C of the present invention, an intrachain disulfide linkage is formed between the 29th cysteine residue and the 52nd cysteine residue, while interchain disulfide linkages are formed between the 77th cysteine residues of two curculin C monomer chains and between the 109th cysteine residues of two curculin C monomer chains, thus giving a dimer, and the monomer has an amino acid sequence as specified in the following sequence list:

| Sequence list: |
|---|
| Asp Asn Val Leu Leu Ser Gly Gln Thr Leu His Ala Asp His Ser 15 |
| Leu Gln Ala Gly Ala Tyr Thr Leu Thr Ile Gln Asn Lys Cys Asn 30 |
| Leu Val Lys Tyr Gln Asn Gly Arg Gln Ile Trp Ala Ser Asn Thr 45 |
| Asp Arg Arg Gly Ser Gly Cys Arg Leu Thr Leu Leu Ser Asp Gly 60 |
| Asn Leu Val Ile Tyr Asp His Asn Asn Asn Asp Val Asn Gly Ser 75 |
| Ala Cys Trp Gly Asp Asn Gly Lys Tyr Ala Leu Val Leu Gln Lys 90 |
| Asp Gly Arg Phe Val Ile Tyr Gly Pro Val Leu Trp Ser Leu Gly 105 |
| Pro Asn Gly Cys Arg Arg Val Asn Gly 114 (SEQ ID NO:1) |

The curculin C of the present invention is a sweetness-inducing substance and can be properly added to, for example, foods, drinks, feeds, pet foods and drugs as a sweetener which occurs as a stable dimer and has a potent taste-modification effect.

Since the amino acid sequence of the curculin C of the present invention has been already determined, it can be produced on a mass scale by chemical or genetic engineering techniques, which is highly advantageous.

DETAILED DESCRIPTION OF THE INVENTION

Curculin C of the present invention can be obtained by, for example, the following method.

First, water is added to Curculigo latifolia fruits or the sarcocarp thereof and the mixture is homogenized and centrifuged. The supernatant thus obtained has a dark brown color. Further, water as much as, or more than the starting fruits or sarcocarp is added to the precipitate and the resulting mixture is homogenized and centrifuged. Water-washing is repeated until a colorless supernatant is obtained. Thus a precipitate is obtained. None of the supernatants show any taste-modification activity.

Next, the precipitate obtained above is extracted with an aqueous solution of a salt having a concentration of 0.01M or above. Thus a crude extract containing a curculin C is obtained.

Examples of the salt include hydrochlorides of sodium, potassium, calcium, magnesium and ammonium, phosphates of sodium, potassium, calcium, magnesium and ammonium, carbonates of sodium, potassium, calcium, magnesium and ammonium, sulfates and sulfites of sodium, potassium, calcium, magnesium and ammonium, nitrates and nitrites of sodium and potassium, lactates of sodium and calcium, alum, burnt alum, sodium acetate, pyrophosphates of sodium and potassium, propionates of sodium and potassium, sodium benzoate, sodium fumarate and polysodium acrylate.

The extraction with the aqueous salt solution as described above may be effected, for example, as follows.

After the completion of the above-mentioned washing with water, a sodium chloride solution is added to the precipitate thus obtained, and the mixture is homogenized, centrifuged or filtered to thereby give a crude extract containing a curculin C.

Next, the crude extract containing the curculin C thus obtained is purified in the following manner so as to give a taste-modifier of a high purity.

The above-mentioned crude extract may be purified by salting out with, for example, ammonium sulfate, sodium sulfate, potassium phosphate, magnesium sulfate, sodium citrate or sodium chloride and treating by common chromatographic procedures. For example, the precipitate obtained by salting out with ammonium sulfate is subjected to CM-Sepharose ion exchange chromatography followed by molecular sieve chromatography. Thus the target curculin C of a high purity can be obtained.

The amino acid sequence (primary structure) of the highly pure curculin C thus obtained may be determined by reducing the highly pure substance, blocking the SH group thereof, hydrolyzing with an enzyme such as trypsin, chymotrypsin or lysyl-endopeptidase, purifying each peptide fragment by HPLC using an aqueous reversed-phase column and then determining the structure of the peptide fragment.

Curculin C, which consists of a dimer of a protein, is obtained in the form of a stable protein having a high taste-modification activity. The dimer is obtained by forming interchain disulfide linkages between the 77th cysteine residues and between the 109th cysteine residues.

The interchain linkage is identified by fragmentating the highly pure curculin C with the use of various proteases such as thermolysin or trypsin, purifying a peptide fragment containing cystine from among the obtained fragments by, for example, HPLC, determining the structure of this peptide fragment and comparing it with the primary structure.

In the monomer of the curculin C of the present invention, furthermore, the 29th cysteine residue forms an intrachain disulfide linkage with the 52nd cysteine residue.

This intrachain linkage is identified in the same manner as the one described above regarding the interchain linkage.

Namely, it is identified by fragmentating the highly pure curculin C with the use of various proteases such as thermolysin or trypsin, purifying a peptide fragment containing cystine from among the obtained fragments by, for example, HPLC, determining the structure of this peptide fragment and comparing it with the primary structure.

Curculin C thus obtained can be used as a taste-modifier. Further, it is preferable that the highly pure curculin C is used in the form of a liquid seasoning of a concentration of $10^{-7}$M or above or a solid seasoning of a concentration of 10 ppm w/w % or above.

The highly pure curculin C according to the present invention, which has the above-mentioned amino acid sequence, may be synthesized by an appropriate method, for example, solid-phase synthesis, partial solid-phase synthesis, fragment condensation or solution synthesis, in accordance with the amino acid sequence. Alternately, it may be obtained by recombinant DNA techniques with the use of a suitable host.

Example 1: Water-washing and Extraction with Sodium Chloride Solution 30 g of the sarcocarp of Curculigo latifolia fruits was homogenized together with 40 ml of water and then centrifuged at 12,500 r.p.m for 60 minutes. The obtained supernatant had a dark brown color and showed no taste-modification activity. To the obtained precipitate was added 40 ml of water and the mixture was homogenized and centrifuged at 12,500 r.p.m. for 20 minutes. The obtained supernatant was colorless and had no taste-modification activity.

To the obtained precipitate was added a 0.5M sodium chloride solution and the mixture was homogenized and centrifuged at 30,000 r.p.m. for 60 minutes. The supernatant thus obtained was colorless and showed a taste-modification activity. Further, extraction with 40 ml of a 0.5M sodium chloride solution was repeated twice. Then the supernatants were combined to thereby give a crude extract containing a curculin C.

Example 2: Salting Out with Ammonium Sulfate

To the crude extract obtained in the above Example 1 was added ammonium sulfate so as to achieve an 80%-saturation, thus precipitating an active substance. After centrifuging at 32,000 r.p.m. for 60 minutes, the precipitate thus obtained was dissolved in 100 ml of a 0.01M phosphate buffer solution (pH: 6.8).

Example 3: CM-Sepharose Ion Exchange Chromatography

The solution obtained in the above Example 2 was applied to a CM-Sepharose CL-6B column [2.2 cm (diameter)×18 cm (length), bed volume: 68 ml, the matrix being a cross-linked derivative of beaded agarose, with a carboxymethyl functionality and with cross-links between polysaccharide chains formed by the reaction of the base matrix with 2,3-dibromopropanol, manufactured by Pharmacia LKB Biotechnology Co.] and adsorbed thereon.

After removing a bypass fraction with a 0.01M phosphate buffer solution (pH: 6.8), the curculin C was eluted by linear gradient elution with a 0–1.0M sodium chloride solution (flow rate: 5 ml/hr, fraction volume: 5 ml, total eluate volume: 500 ml).

Figure 1:
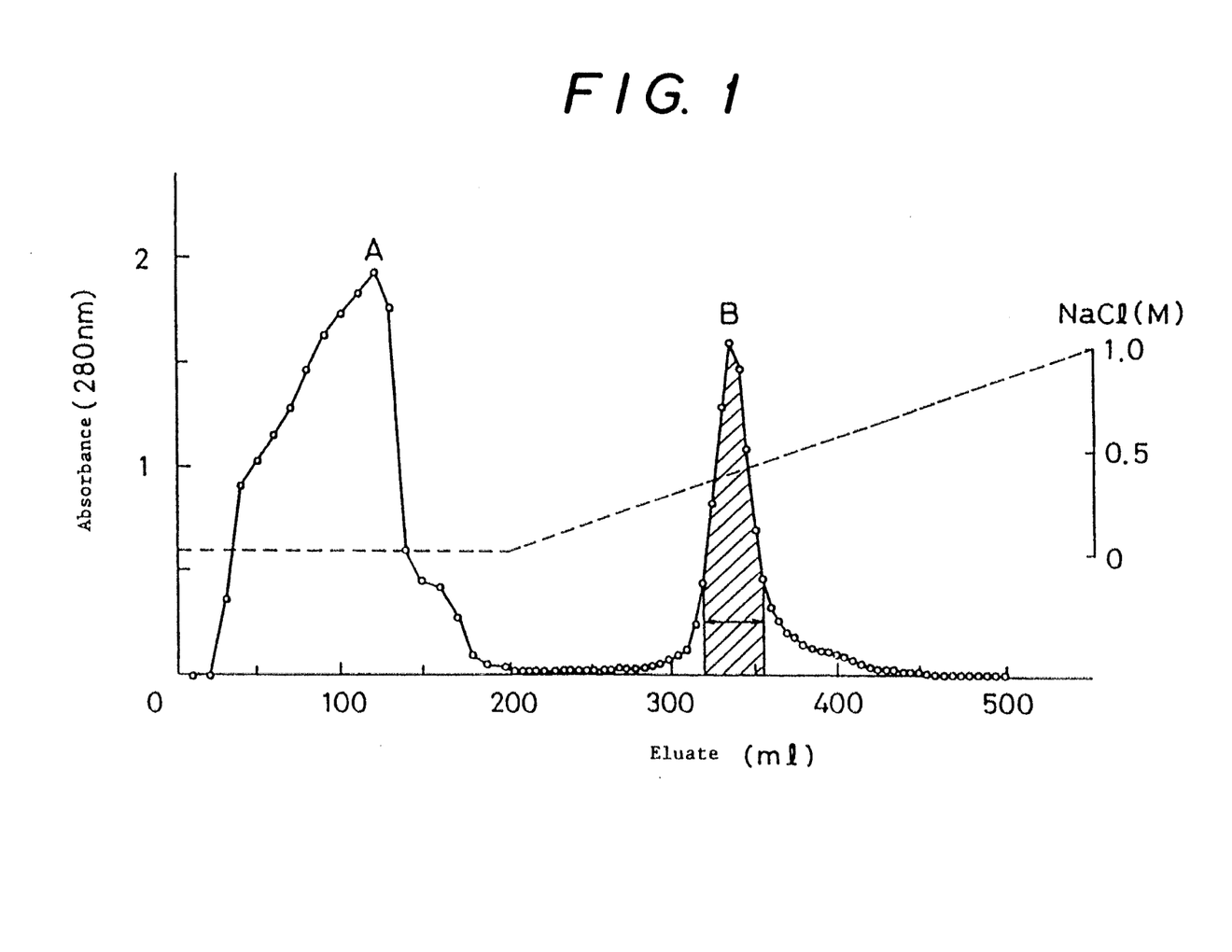
FIG. 1 is a CM-Sepharose ion exchange chromatography elution pattern of a curculin C which is obtained from Curculigo latifolia fruits through washing with water, extracting and salting out.

The proteins thus eluted were monitored by using the absorbance at 280 nm. FIG. 1 shows the result. The peak (B) shown in FIG. 1 corresponds to fractions containing the curculin C.

Example 4: Gel Filtration Chromatography

To the fractions corresponding to the hatched part of the peak (B) in FIG. 1 was added ammonium sulfate so as to achieve an 80%- saturation, thus precipitating the active substance. After centrifuging at 32,000 r.p.m. for 60 minutes, the obtained precipitate was dissolved in 1.5 ml of a 0.01M phosphate buffer solution (pH: 6.8).

This concentrate was separated with the use of a Sephadex (a beaded gel prepared by cross-linking dextran with epichlorohydrin under alkaline conditions, manufactured by Pharmacia LKB Biotechnology Co.) G-100 column [1.6 cm (diameter)×58 cm (length), bed volume: 160 ml] and a 0.01M phosphate buffer solution (pH: 6.8) containing 0.5M NaCl (flow rate: 8.4 ml/hr, fraction volume: 2.8 ml, total eluate volume: 182 ml).

Figure 2:
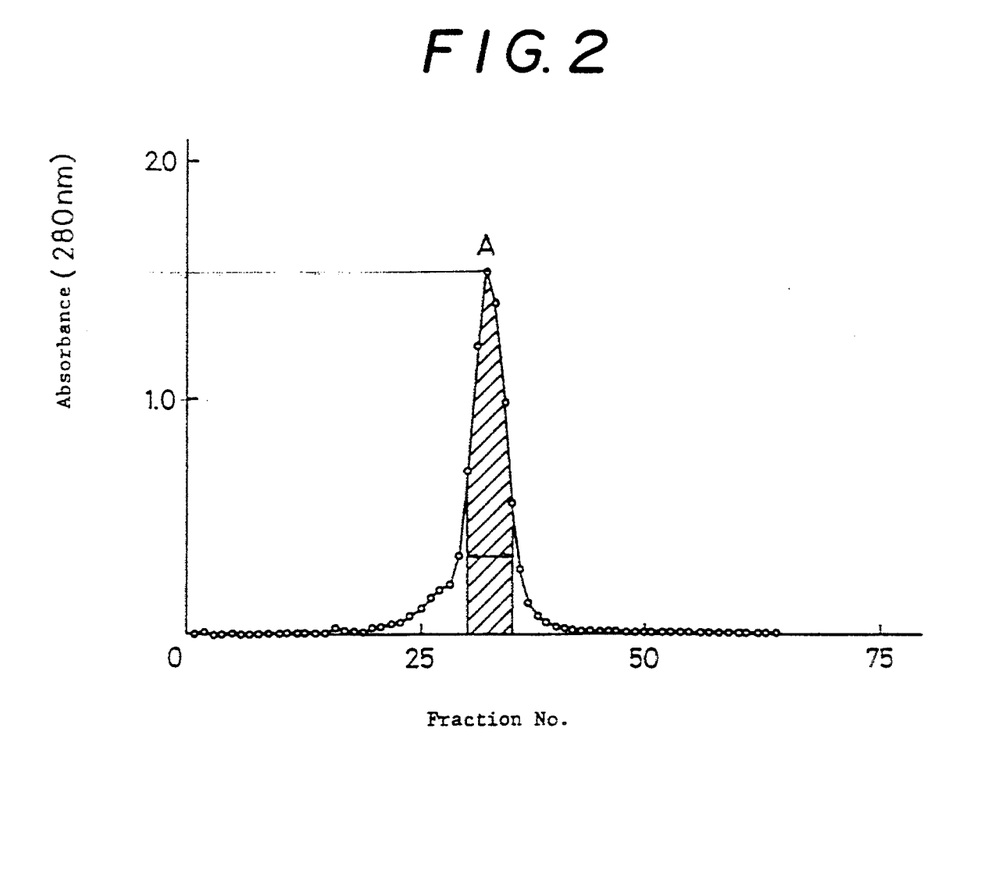
FIG. 2 is a Sephadex G-100 molecular sieve chromatography elution pattern of the peak (B) in FIG. 1.

The proteins were monitored with the use of the absorbance at 280 nm. FIG. 2 shows the result. The peak (A) shown in FIG. 2 Corresponds to fractions containing the curculin C.

To the fractions corresponding to the peak (A) in FIG. 2 was added ammonium sulfate so as to achieve an 80%- saturation, thus precipitating the active substance. After centrifuging at 32,000 r.p.m. for 60 minutes, the obtained precipitate was dissolved in 1.5 ml of a 2M ammonium acetate solution. The obtained solution was treated with a Sephadex G-25 (9.1 ml) column equilibrated with a 2M ammonium acetate solution and then freeze-dried. Thus 8.6 mg of a curculin C of a high purity was obtained.

Example 5: SDS-polyacrylamide Gel Electrophoresis

The purity and molecular weight of the highly pure curculin C obtained in the, above Example 4 were confirmed in accordance with Laemmli's method [refer to Nature, 227, 680 (1970)] by SDS polyacrylamide gel electrophoresis with and without using a reducing agent ($\beta$-mercaptoethanol).

As a result, a band corresponding to a molecular weight of 13,000 (dalton) was observed in the presence of the reducing agent, while a band corresponding to a molecular weight of 24,000 (dalton) was observed in the absence thereof.

These results indicated that the highly pure curculin C obtained in the above Example 4 had been sufficiently purified and a dimer had been formed via the formation of disulfide linkages.

Table 1 shows the protein content, activity yield and purity of each fraction obtained from 30 g of the sarcocarp of Curculigo latifolia fruits.

TABLE 1

| Purification step | Protein content, activity yield and purity of curculin C in each purification step | | |
|---|---|---|---|
| | Protein content (g) | Activity yield (%) | Purity (fold) |
| Sarcocarp | 30 (*1) | 100 | 1 |
| 0.5M saline extract | 0.106 | 80.0 | 225 |
| CM-Sepharose eluate | 0.018 | 55.5 | 940 |
| Sephadex G-100 eluate | 0.0086 | 36.0 | 1255 |

*1: sarcocarp weight (including components other than proteins).

The protein contents were determined by the method of Lowry et al.

The taste-modification activity of the highly pure curculin C obtained in the above Example 4 was evaluated in the following manner. After each sample was kept in the mouth for 3 minutes, the mouth was rinsed with water. Then a 0.02M solution of citric acid was tasted and the sweetness was compared with those of sucrose solutions of various concentrations. Thus a sucrose solution showing a sweetness comparative thereto was selected.

Figure 3:
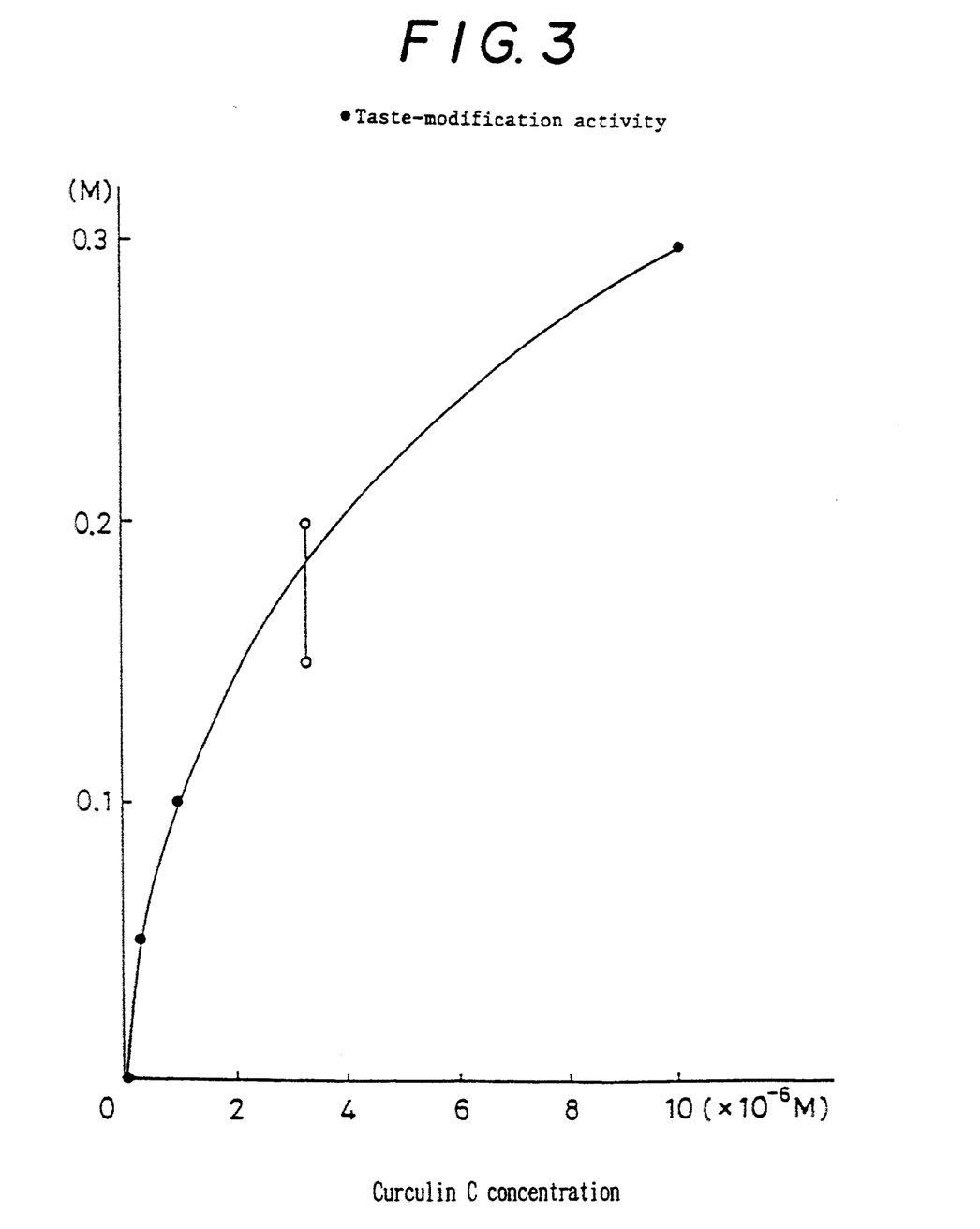
FIG. 3 is a graph showing the activity of curculin C comprising the highly pure taste-modifier according to the present invention.

FIG. 3 shows the results. As this figure shows, the activity of the highly pure curculin C corresponds to the sweetness of a 0.3M sucrose solution. The taste-modification effect of the highly pure curculin C obtained in the Example 4 was sustained for a long period of time.

Referential Example 1: Isoelectric Focusing

The highly pure curculin C obtained in the above Example 4 was subjected to isoelectric focusing with the use of Phast Gel IEF5-8 of Phast System TM (manufactured by Pharmacia LKB Biotechnology Co. ). It was found that the isoelectric point was 7.1.

Referential Example 2: Confirmation of the Absence of any Free SH Group 1.2 mg (50 nmol) of the highly pure curculin C obtained in the above Example 4 was dissolved in 2.5 ml of a 0.1M tris hydrochloride buffer solution (pH: 8.0) containing 8M of urea and 0.01M of EDTA (ethylenediaminetetraacetic acid) and allowed to stand at room temperature for 20 minutes.

Then a 0.05M phosphate buffer solution (pH: 7.0) containing 0.01M DTNB [5,5-dithiobis(2-nitrobenzoic acid)] was added thereto and the absorbances of cysteine and the highly pure curculin C were measured at 412 nm.

The absorbance of 50 nmol of the highly pure curculin C was 0.005 or below when measured under such a condition that the absorbance of 50 nmol of cysteine was 0.25.

These facts indicated that no free SH group was contained in the molecule of the highly pure curculin C.

Example 6: Preparation of S-carboxamidomethylated Curculin C.

7 mg of the highly pure curculin C obtained in the above Example 4 was dissolved in 5 ml of a 0.4M tris buffer solution containing 6M of guanidine hydrochloride, 2 mM of EDTA and 60 mM of dithiotheritol. The obtained solution was incubated in a nitrogen gas at 37° C. for 24 hours. Next, 0.2 g of iodoacetamide was added to the solution. After allowing to stand at room temperature for 10 minutes, the mixture was further allowed to stand in an ice/water bath for 60 minutes. The S-carboxamidomethylated curculin C thus obtained was subjected to buffer exchange with a 50 mM sodium bicarbonate buffer solution (pH: 8.0) containing 2M of urea and 2 mM of EDTA by using Sephadex G-25 to thereby give a sample to be digested with an enzyme.

Example 7: Amino Acid Composition

The amino acid composition was determined with a Picotag system (manufactured by Waters Co.).

Namely, 10 $\mu$g of the highly pure curculin C obtained in the above Example 4 was hydrolyzed with 6 N HCl containing 1% of phenol at 110° C. for 22 hours. Then the amino acids thus obtained were phenylthiocarbamylated (PTC) and analyzed by HPLC with the use of a TSK gel ODS-80TM column [0.46 cm (diameter)×15 cm (length), manufactured by Tosoh Corp.]. The PTC-amino acids were detected based on the absorbance at 254 nm. Table 2 shows the results.

The data of serine and threonine were corrected by taking the loss due to decomposition, respectively, as 10% and 5%. Regarding cysteine, the S-carboxamidomethylated curculin C prepared in the above Example 6 was employed in the measurement. On the other hand, the content of tryptophan was determined by the method of H. Edelhock [refer to Biochemistry, 7, 1948 (1967)].

TABLE 2

| Amino acid composition | | | |
|---|---|---|---|
| Amino acid | % by mol | Amino acid | % by mol |
| Asx | 17.2 | Met | 0.4 |
| Thr | 5.0 | Ile | 3.9 |
| Ser | 6.6 | Leu | 13.6 |
| Glx | 5.9 | Tyr | 4.9 |
| Pro | 1.1 | Phe | 1.2 |
| Gly | 11.7 | Lys | 2.9 |
| Ala | 5.0 | His | 2.2 |
| Half-cys | 4.0 | Arg | 5.7 |
| Val | 6.4 | trp | 2.3 |
| Total | | | 100.0 |

Example 8: Enzymatic Digestion of S-carboxamidomethylated Curculin C

The S-carboxamidomethylated curculin C obtained in the above Example 6 was digested with lysylendopeptidase in a 50 mM sodium bicarbonate buffer solution (pH: 8.0) containing 2M of urea and 2 mM of EDTA at 37° C. for 17.5 hours. The protein concentration was 1 mg/ml and the enzyme to substrate ratio was 1/120. Then the reaction was terminated by adjusting the pH value of the mixture to 2.0 by HCl.

Further, the S-carboxamidomethylated curculin C was digested with chymotrypsin at 37° C. for 30 minutes under the same conditions of buffer solution, protein concentration and enzyme to substrate ratio as those employed above. The reaction was terminated by the same method as the one described above.

Furthermore, the S-carboxamidomethylated curculin C was digested with trypsin at 37° C. for 3 hours under the same conditions of buffer solution, protein concentration and enzyme to substrate ratio as those employed above. The reaction was terminated by the same method as the one described above.

Example 9: Isolation of Peptide

The three peptide mixtures obtained in the above Example 8 were separated by HPLC with the use of a TSK gel ODS-120T (manufactured by Tosoh Corp.) column. Then each peptide was eluted by linear gradient elution with acetonitrile containing 0.05% of trifluoroacetic acid. The peptide was detected based on the absorbance at 210 nm and each peak was collected.

Figure 4:
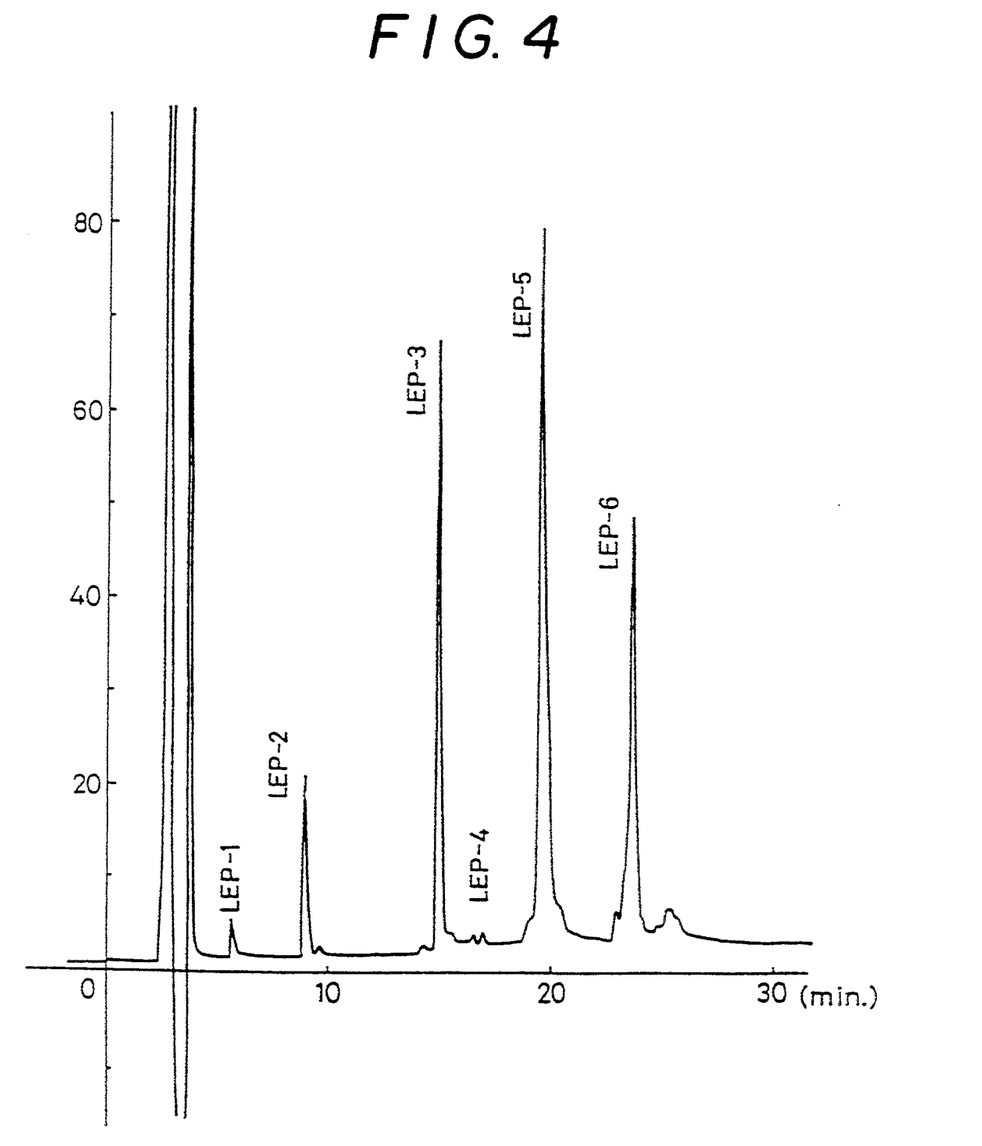
FIG. 4 is an HPLC elution pattern of a peptide obtained by digesting S-carboxamidomethylated curculin C with lysyl-endopeptidase.
Figure 5:
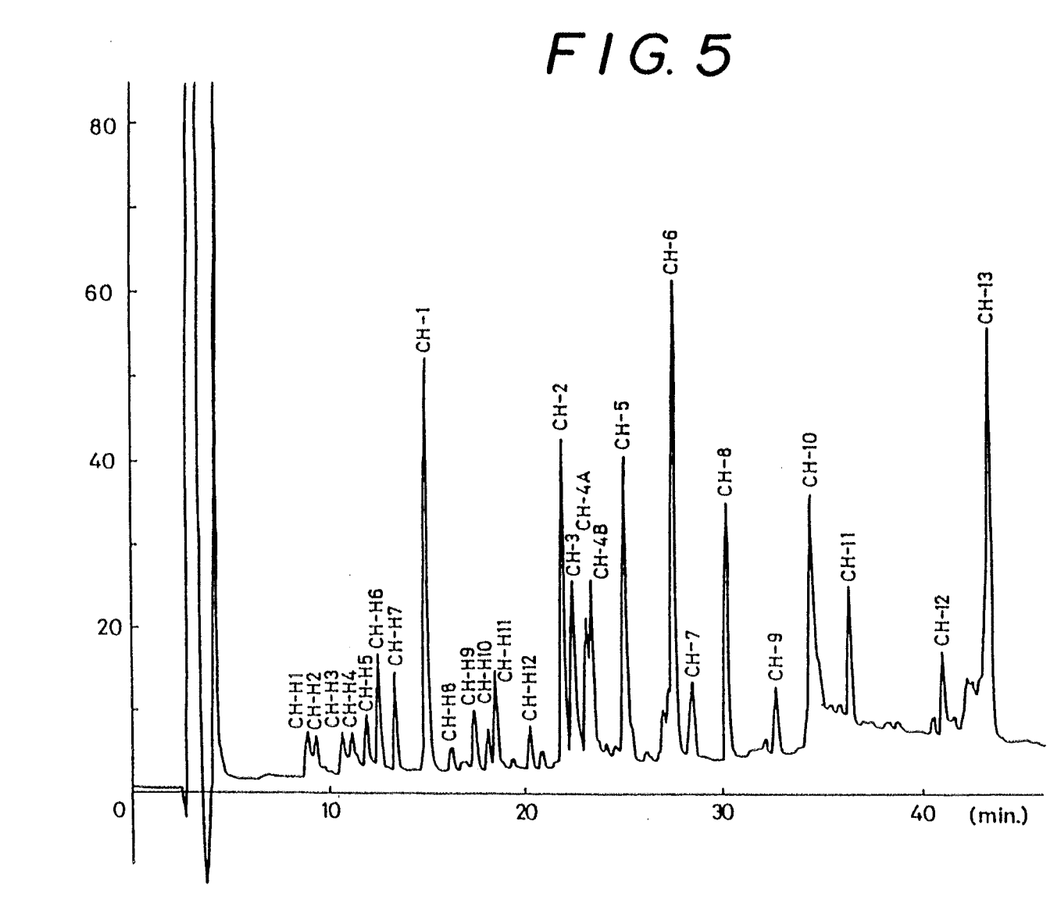
FIG. 5 is an HPLC elution pattern of a peptide obtained by digesting S-carboxamidomethylated curculin C with chymotrypsin.
Figure 6:
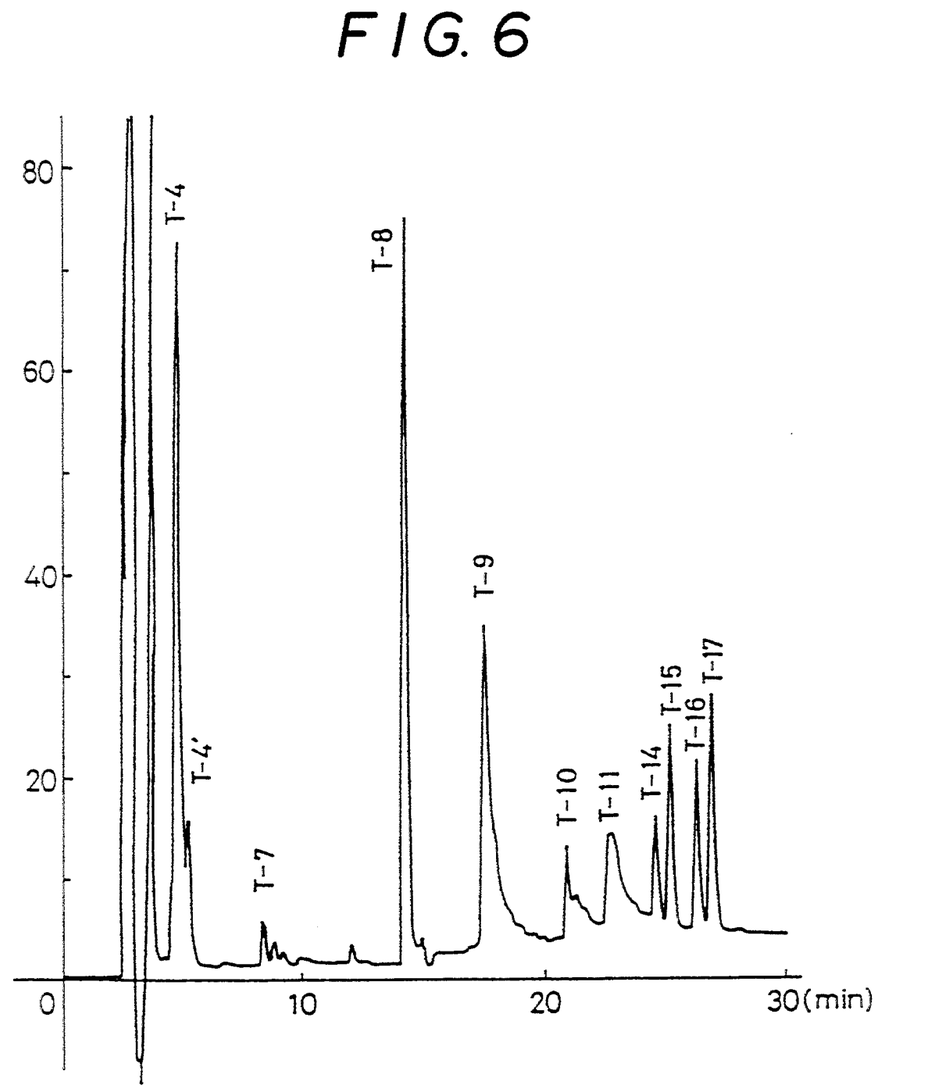
FIG. 6 is an HPLC elution pattern of a peptide obtained by digesting S-carboxamidomethylated curculin C with trypsin.

FIG. 4, FIG. 5 and FIG. 6 show the elution patterns of, respectively, peptide mixtures obtained by lysyl-endopeptidase digestion, peptide mixtures obtained by chymotrypsin digestion and peptide mixtures obtained by trypsin digestion.

It is to be noted here that the elution patterns of peptide mixtures obtained by the lysyl-endopeptidase digestion and peptide mixtures obtained by the trypsin digestion were obtained by linear concentration gradient elution with 20% (v/v, the balance: water) to 40% (v/v, the balance: water) of acetonitrile for 30 minutes, while that of peptide mixtures obtained by the chymotrypsin digestion was eluted by linear gradient elution with 10% (v/v, the balance: water) to 40% (v/v, the balance: water) of acetonitrile for 45 minutes. The names of the peptides which will be given hereinbelow were assigned in accordance with the names of these peaks.

Example 10: Analysis on amino acid composition and Determination of Amino Acid Sequence Each peptide obtained in the above Example 9 was subjected to amino acid analysis with a Waters Picotag system. Tables 3 and 4 show the results.

TABLE 3

Amino acid composition of peptide obtained from lysyl-endopeptidase or trypsin digestion of S-carboxamidomethylated curculin C (unit: mol/mol of peptide)

| Amino acid | LEP-2 | LEP-3 | LEP-5 | LEP-6 | T-11 | Curculin |
|---|---|---|---|---|---|---|
| Asx(B) | | 5.4(5) | 13.0(13) | 2.7(3) | 9.4(10) | (21) |
| Glx(Z) | 1.2(1) | 3.2(3) | 2.4(2) | | 1.4(1) | (6) |
| Cys(C) | | 0.7(1) | 1.4(2) | 0.8(1) | 0.7(1) | (4) |
| Ser(S) | | 2.3(2) | 3.8(4) | 1.1(1) | 2.5(2) | (7) |
| Gly(G) | | 2.6(2) | 6.9(7) | 4.7(5) | 4.4(4) | (14) |
| His(H) | | 2.2(2) | 1.1(1) | | 1.2(1) | (3) |
| Thr(T) | | 3.0(3) | 2.0(2) | | 1.2(1) | (5) |
| Ala(A) | 0.8(1) | 3.4(3) | 2.7(2) | | 2.3(2) | (6) |
| Pro(P) | | | | 2.3(2) | | (2) |
| Arg(R) | | | 3.8(4) | 3.4(3) | | (7) |
| Tyr(Y) | 1.0(1) | 1.0(1) | 1.9(2) | 1.1(1) | 1.9(2) | (5) |
| Val(V) | 1.1(1) | 1.7(2) | 1.7(2) | 2.2(3) | 2.5(3) | (8) |
| Ile(I) | | 1.0(1) | 1.9(2) | 0.7(1) | 0.7(1) | (4) |
| Leu(L) | 2.1(2) | 5.2(6) | 3.8(4) | 2.1(2) | 5.9(6) | (14) |
| Phe(F) | | | | 1.2(1) | | (1) |
| Lys(K) | 0.8(1) | 1.3(2) | 0.9(1) | | 2.3(2) | (4) |
| Trp(W) | | ND(2) | ND(1) | ND(1) | | (3) |
| Total | (7) | (33) | (50) | (24) | (37) | (114) |
| Assignment | 84–90 | 1–33 | 34–83 | 91–114 | 54–90 | |
| Yield % | 55.2 | 72.4 | 83.0 | 68.5 | 31.3 | |

The data of serine and threonine were corrected by taking the loss due to decomposition, respectively, as 10% and 5%.

TABLE 4

Amino acid composition of peptide obtained from chymotrypsin digestion of S-carboxamidomethylated curculin C (unit: mol/mol of peptide)

| Amino acid | CH-H3 | CH-4B | CH-4A | CH-6 | CH-10 | CH-13 |
|---|---|---|---|---|---|---|
| Asx(B) | 2.0(2)(*) | 1.0(1) | 1.6(2) | 3.0(3) | 11.3(12) | 1.4(1) |
| Glx(Z) | | 2.0(2) | 1.0(1) | 1.9(2) | | 0.8(1) |
| Cys(C) | 0.7(1) | | 0.8(1) | | 1.3(2) | |
| Ser(S) | 1.0(1) | | | 2.0(2) | 4.2(4) | |
| Gly(G) | 2.5(3) | 1.1(1) | | 2.1(2) | 6.6(6) | 2.2(2) |
| His(H) | | | | 1.8(2) | 1.2(1) | |
| Thr(T) | | | 1.6(2) | 1.1(1) | 1.7(2) | |
| Ala(A) | | | | 3.1(3) | 2.4(2) | 0.7(1) |
| Pro(P) | 1.3(1) | | | | | 1.2(1) |
| Arg(R) | 1.8(2) | 1.1(1) | | | 3.3(3) | 1.3(1) |
| Tyr(Y) | | | 1.0(1) | 1.0(1) | 2.3(2) | 1.2(1) |
| Val(V) | 1.2(1) | | 2.1(1) | 0.9(1) | 1.9(2) | 2.4(3) |
| Ile(I) | | 0.8(1) | 0.7(1) | | 1.1(1) | 1.0(1) |
| Leu(L) | 1.3(1) | | 1.3(2) | 4.2(4) | 4.5(4) | 2.7(3) |
| Phe(F) | | | | | | 1.0(1) |
| Lys(K) | | | 1.7(2) | | 0.9(1) | 0.7(1) |
| Trp(W) | | ND(1)(**) | | | ND(1) | ND(1) |
| Total | (12) | (7) | (13) | (21) | (43) | (18) |

TABLE 4-continued

Amino acid composition of peptide obtained from chymotrypsin digestion of S-carboxamidomethylated curculin C
(unit: mol/mol of peptide)

| Amino acid | CH-H3 | CH-4B | CH-4A | CH-6 | CH-10 | CH-13 |
|---|---|---|---|---|---|---|
| Assignment | 103–114 | 35–41 | 22–34 | 1–21 | 42–84 | 85–102 |
| Yield % | 6.1 | 18.9 | 17.5 | 38.1 | 15.0 | 19.3 |

*: Result of sequence analysis.
**: ND: not detected.

The data of serine and threonine were corrected by taking the loss due to decomposition, respectively, as 10% and 5%.

The amino acid sequence was determined with the use of a 470 A Applied Biosystem Protein Sequencer.

Namely, the peptide was degraded by Edman method and the resulting PTH (phenylthiohydantoin)-amino acid was analyzed by HPLC with the use of a TKS gel ODS-120T column. Table 5 and 6 show the results.

TABLE 5

Amino acid residues identified by Edman degradation of peptides obtained from lysyl-endopeptidase digestion and trypsin digestion of S-carboxamidomethylated curculin C

| Cycle | LEP-2 Amino acid (Yield) (p mole) | LEP-3 Amino acid (Yield) (p mole) | LEP-5 Amino acid (Yield) (p mole) | LEP-6 Amino acid (Yield) (p mole) | T-11 Amino acid (Yield) (p mole) | N Amino acid (Yield) (p mole) |
|---|---|---|---|---|---|---|
| 1 | Tyr(3060) | Asp(861) | Tyr(405) | Asp(244) | Leu(1383) | Asp(264) |
| 2 | Ala(4103) | Asn(671) | Gln(496) | Gly(856) | Thr(447) | Asn(146) |
| 3 | Leu(2016) | Val(606) | Asn(50) | Arg(72) | Leu(1053) | Val(232) |
| 4 | Val(1987) | Leu(495) | Gly(139) | Phe(866) | Leu(1344) | Leu(106) |
| 5 | Leu(901) | Leu(703) | Arg(56) | Val(1005) | Ser(346) | Leu(118) |
| 6 | Gln(1351) | Ser(85) | Gln(138) | Ile(682) | Asp(937) | Ser(15) |
| 7 | Lys(489) | Gly(227) | Ile(171) | Tyr(623) | Gly(864) | Gly(35) |
| 8 | | Gln(482) | Trp(92) | Gly(457) | Asn(1028) | Gln(96) |
| 9 | | Thr(120) | Ala(156) | Pro(301) | Leu(615) | Thr(16) |
| 10 | | Leu(277) | Ser(28) | Val(273) | Val(730) | Leu(77) |
| 11 | | His(146) | Asn(114) | Leu(196) | Ile(504) | His(28) |
| 12 | | Ala(338) | Thr(44) | Trp(40) | Tyr(797) | Ala(60) |
| 13 | | Asp(443) | Asp(151) | Ser(86) | Asp(844) | Asp(78) |
| 14 | | His(67) | Arg(69) | Leu(199) | His(204) | His(13) |
| 15 | | Ser(22) | Arg(86) | Gly(216) | Asn(609) | Ser(7) |
| 16 | | Leu(154) | Gly(75) | Pro(213) | Asn(758) | Leu(33) |
| 17 | | Gln(133) | Ser(15) | (Asn) | Asn(809) | Gln(21) |
| 18 | | Ala(119) | Gly(63) | Gly(105) | Asp(603) | Ala(23) |
| 19 | | Gly(81) | Cys(57) | Cys(66) | Val(281) | Gly(32) |
| 20 | | Ala(58) | Arg(56) | Arg(21) | Asn(264) | Ala(31) |
| 21 | | Tyr(57) | Leu(79) | Arg(27) | Gly(298) | |
| 22 | | Thr(24) | Thr(26) | Val(12) | Ser(193) | |
| 23 | | Leu(77) | Leu(68) | | Ala(201) | |
| 24 | | Thr(17) | Leu(72) | | Cys(150) | |
| 25 | | Ile(44) | Ser(9) | | Trp(27) | |
| 26 | | | Asp(84) | | Gly(148) | |
| 27 | | | Gly(38) | | Asp(204) | |
| 28 | | | Asn(51) | | Asn(31) | |
| 29 | | | Leu(46) | | Gly(72) | |
| 30 | | | Val(28) | | Lys(17) | |
| 31 | | | Ile(30) | | Tyr(28) | |
| 32 | | | Tyr(20) | | Ala(38) | |
| 33 | | | Asp(69) | | Leu(7) | |
| 34 | | | His(7) | | Val(53) | |

TABLE 6

Amino acid residues identified by Edman degradation of peptides obtained from chymotrypsin digestion of S-carboxamidomethylated curculin C

| Cycle | CH-H3 Amino acid (Yield) (p mole) | CH-4B Amino acid (Yield) (p mole) | CH-4A Amino acid (Yield) (p mole) | CH-6 Amino acid (Yield) (p mole) | CH-10 Amino acid (Yield) (p mole) | CH-13 Amino acid (Yield) (p mole) |
|---|---|---|---|---|---|---|
| 1 | Ser(1687) | Gln(81) | Thr(179) | Asp(2395) | Ala(443) | Ala(227) |
| 2 | Leu(2813) | Asn(71) | Leu(553) | Asn(2047) | Ser(74) | Leu(116) |
| 3 | lGly(2198) | Gly(66) | Thr(147) | Val(1793) | Asn(251) | Val(141) |
| 4 | Pro(2673) | Arg(10) | Ile(137) | Leu(941) | Thr(46) | Leu(101) |
| 5 | Asn(2401) | Gln(63) | Gln(235) | Leu(1165) | Asp(133) | Gln(112) |
| 6 | Gln(1596) | Ile(60) | Asn(175) | Ser(132) | Arg(53) | Lys(68) |
| 7 | Cys(2302) | Trp(6) | Lys(152) | Gly(582) | Arg(93) | Asp(96) |
| 8 | Arg(1553) | | Cys(188) | Gln(797) | Gly(85) | Gly(93) |
| 9 | Arg(1735) | | Asn(161) | Thr(273) | Ser(32) | Arg(30) |
| 10 | Val(1547) | | Leu(45) | Leu(596) | Gly(60) | Phe(39) |
| 11 | Asn(862) | | Val(37) | His(278) | Cys(65) | Val(74) |
| 12 | Gly(150) | | Lys(7) | Ala(713) | Arg(21) | Ile(20) |

TABLE 6-continued

Amino acid residues identified by Edman degradation of peptides obtained from chymotrypsin digestion of S-carboxamidomethylated curculin C

| Cycle | CH-H3 Amino acid (Yield) (p mole) | CH-4B Amino acid (Yield) (p mole) | CH-4A Amino acid (Yield) (p mole) | CH-6 Amino acid (Yield) (p mole) | CH-10 Amino acid (Yield) (p mole) | CH-13 Amino acid (Yield) (p mole) |
|---|---|---|---|---|---|---|
| 13 | | | Tyr(9) | Asp(881) | Leu(47) | Tyr(32) |
| 14 | | | | His(149) | Thr(12) | Gly(41) |
| 15 | | | | Ser(58) | Leu(68) | Pro(11) |
| 16 | | | | Leu(321) | Leu(74) | Val(7) |
| 17 | | | | Gln(230) | Ser(8) | Leu(3) |
| 18 | | | | Ala(330) | Asp(17) | Trp(3) |
| 19 | | | | Gly(187) | Gly (11) | |
| 20 | | | | Ala(341) | Asn(13) | |
| 21 | | | | Tyr(118) | Leu(24) | |
| 22 | | | | | Val(6) | |
| 23 | | | | | Ile(3) | |
| 24 | | | | | Tyr(3) | |
| 25 | | | | | Asp(13) | |

The carboxyl-terminal amino acid sequence was determined by using carboxypeptidase by the following method.

Namely, 200 μg of the highly pure curculin C obtained in the above Example 4 was dissolved in 0.9 ml of an N-ethylmorpholineacetate buffer solution (pH: 8.0).

To the obtained solution was added 10 μg of carboxypeptidase A and the reaction mixture was incubated at room temperature. Some portions of the reaction mixture were sampled 15, 30, 60 and 120 minutes after the initiation of the incubation. Trichloroacetic acid was added to each sample to thereby precipitate proteins. After removing the precipitate, amino acids contained in the supernatant were analyzed with a Waters Picotag system. As a result, it was clarified that the carboxyl-terminal amino acid residue was glycine.

Figure 7:
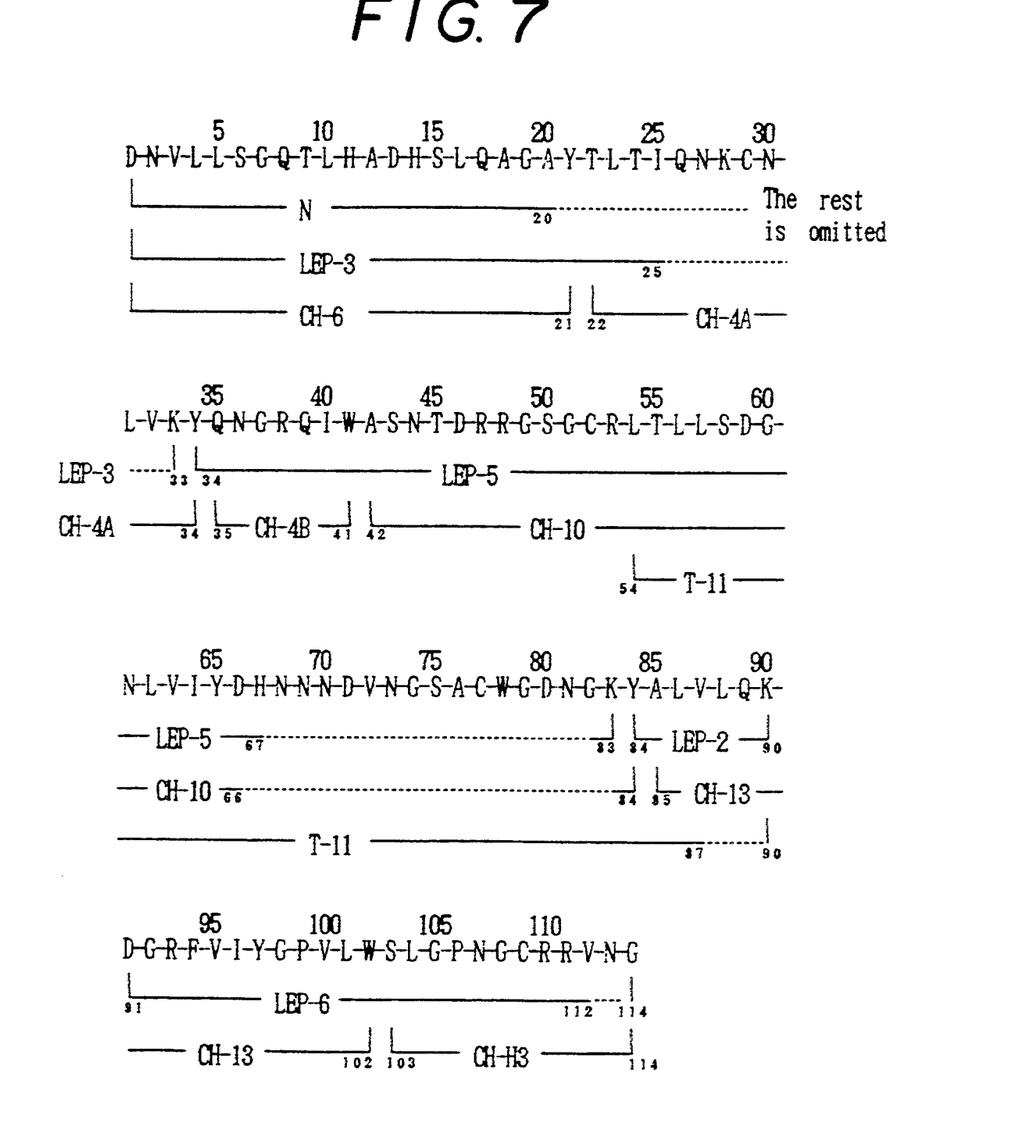
FIG. 7 shows the amino acid sequence of curculin C.

FIG. 7 shows the amino acid sequence determined by the above-mentioned method.

In FIG. 7, LEP, CH and T represent peptides obtained by digesting with, respectively, lysyl-endopeptidase, chymotrypsin and trypsin, while N represents the amino acid sequence of the highly pure curculin C determined by Edman degradation starting with the N-terminal.

A solid line shows the amino acid residues of each peptide which were identified by Edman degradation, while a dotted line shows the amino acid residues of each peptide which were not identified by Edman degradation.

Example 11: Analysis on Amino Acid Composition containing Cysteine or Cystine by Performic Acid Oxidation Method 0.1 ml of a 30% aqueous solution of hydrogen peroxide was added to 1.9 mg of formic acid to thereby give a performic acid solution. Next, 50 μl of this solution was added to the highly pure curculin C or the peptide fragments (0.5 nmol–1 nmol) obtained by digesting with enzymes to conduct a reaction at 0° C. for 25 hours.

After the completion of the reaction, the performic acid solution was dried and subjected to amino acid analysis with the use of a Waters Picotag system. Thus amino acid compositions containing cysteine or cystine described in the following Examples 12 to 14 were determined.

Example 12: Determination of Intrachain Disulfide Linkage between the 29th Cysteine Residue and the 52nd Cysteine Residue The highly pure curculin C obtained in the above Example 4 was digested with trypsin. Namely, 0.5 mg of the highly pure curculin C was dissolved in 200 μl of a 0.25M ammonium acetate buffer solution (pH: 6.5) containing 8M of urea and 2 mM of calcium acetate and denatured therein at 37° C. for 4 hours.

Next, this solution was diluted with a 0.25M ammonium acetate buffer solution (pH.: 6.5) containing 2 mM of calcium acetate in such a manner as to adjust the final urea concentration to 2M.

Figure 8:
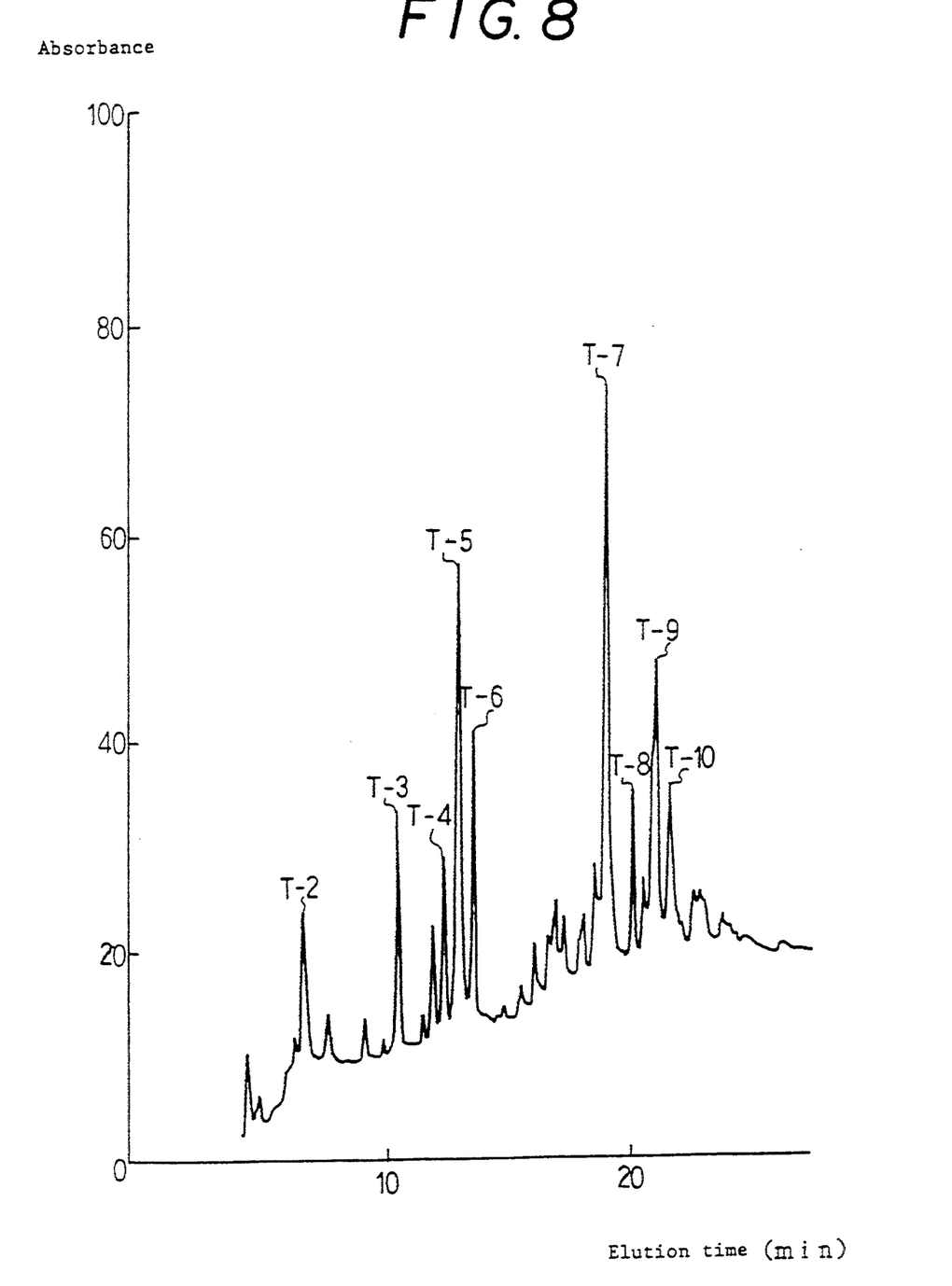
FIG. 8 is an HPLC elution pattern of a peptide obtained by digesting the highly pure curculin C with trypsin.

To the resulting solution of the highly pure curculin C was added trypsin so as to give an enzyme to substrate ratio (by weight) of 1/25. After digesting at 37° C. for 3 hours, the digested mixture was subjected to HPLC under the following conditions to thereby collect each peptide. FIG. 8 shows the results.

Conditions for HPLC:
column: TSK gel ODS-120T,
mobile phase: Aqueous solution of acetonitrile containing 0.05% trifluoroacetic acid (linear concentration gradient from 10% v/v to 60% v/v, 40 minutes),
detection: UV detector 210 nm (rage: 0.5), and
flow rate: 1 ml/min.

The amino acid composition and the amino acid sequence of the substance corresponding to the fraction T2 shown in FIG. 8, from among the peptides thus obtained, were analyzed by the same methods as those described in the above Example 10. Tables 7 and show the results.

TABLE 7

Analysis on amino acid composition of peptide T2 (unit: mol/mol of peptide)

| Amino acid | Asn | Ser | Gly | Arg | Val | Leu | Lys |
|---|---|---|---|---|---|---|---|
| | 0.9 | 1.0 | 2.1 | 0.6 | 1.1 | 1.2 | 0.7 |

TABLE 8

Analysis on amino acid sequence of peptide T2 (unit: pmol)

| Cycle | 1 | 2 | 3 | 4 | 5 |
|---|---|---|---|---|---|
| Amino (p mole) | Gly 481 | Ser 168 Asn | Gly 401 Leu | Cystine 7 Val | Arg 69 Lys |

TABLE 8-continued

Analysis on amino acid sequence of peptide T2 (unit: pmol)

| Cycle | 1 | 2 | 3 | 4 | 5 |
|---|---|---|---|---|---|
|  |  | 289 | 416 | 401 | 181 |

Thus it was confirmed that an intrachain linkage was formed between the 29th cysteine residue and the 52nd cysteine residue.

Example 13: Determination of the Position of Interchain Linkage between 77th Cysteine residues The highly pure curculin C obtained in the above Example 4 was digested with thermolysin.

Namely, 10 mg of the highly pure curculin C was dissolved in a 0.2.5M ammonium acetate buffer solution (pH: 6.5) containing 8M of urea and 2 mM of calcium acetate.

Thermolysin was added to a 0.25M ammonium acetate buffer solution (pH: 6.5) containing 2 mM of calcium acetate and dissolved therein.

To the above-mentioned solution containing the highly pure curculin C was added the thermolysin solution so as to give an enzyme to substrate ratio (by weight) of 1/25, followed by digesting at 37° C. for 15 hours.

Figure 9:
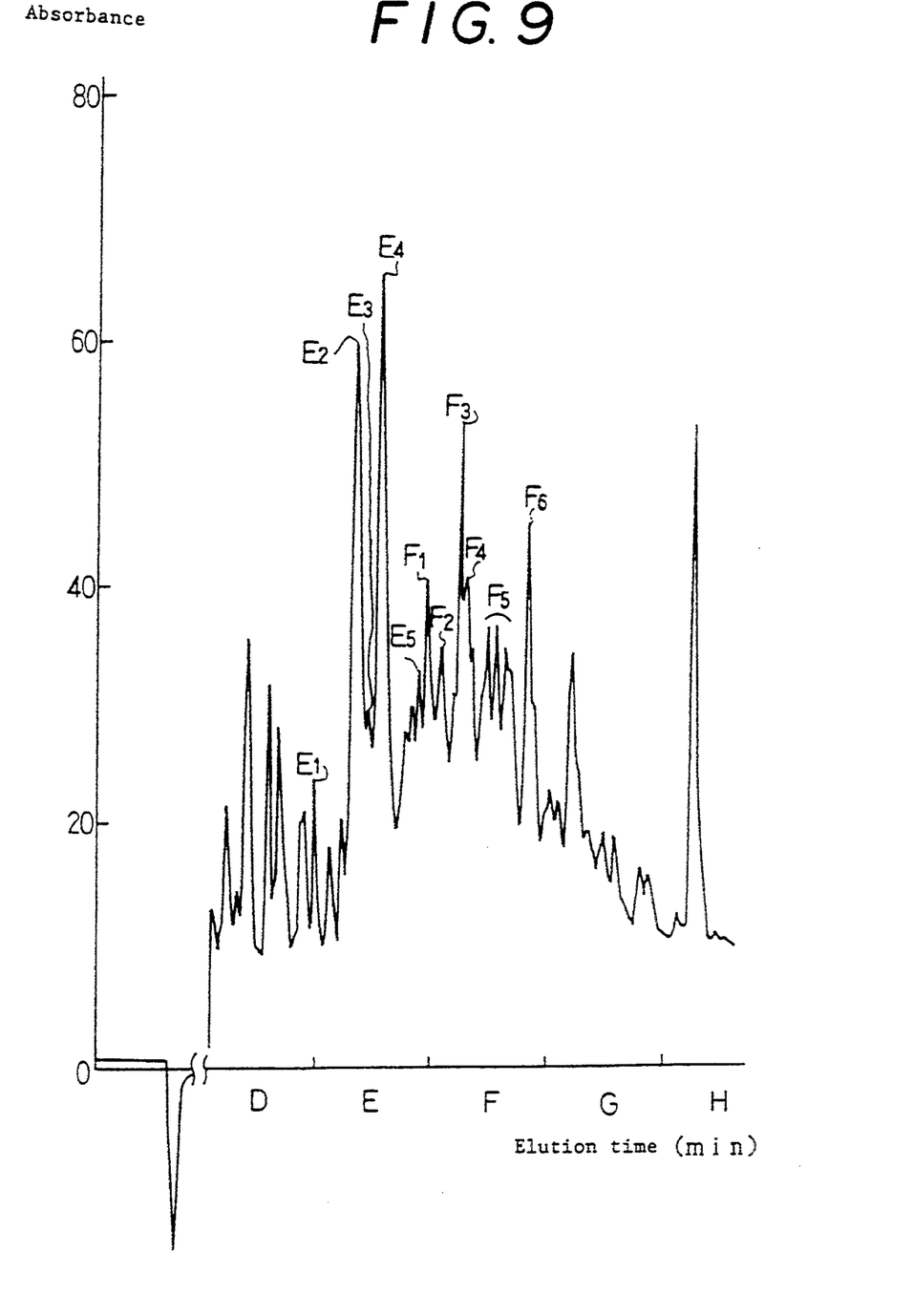
FIG. 9 is an HPLC elution pattern of a peptide obtained by digesting the highly pure curculin C with thermolysin.

Then the digested mixture was subjected to HPLC under the following conditions to thereby collect the peptide corresponding to each peak. FIG. 9 shows the results. Conditions for HPLC:

column: TSK gel ODS-120T, mobile phase: aqueous solution of acetonitrile containing 0.05% trifluoroacetic acid (linear gradient from 10% v/v to 60% v/v, 40 minutes), detection: UV detector 210 nm (range 0.5), and flow rate: 1 ml/min.

Subsequently, the amino acid composition of the peptide of each peak was analyzed by the same method as the one employed in the above Example 11. As a result, cysteic acid was detected from the fraction of the peak E4 shown in FIG. 9 (0.30 pmol/mol). Thus the fraction of the peak E4 was further separated by HPLC.

The separation was carried out under the same conditions as those of the above HPLC except that the mobile phase was eluted by linear gradient with acetonitrile of 20% v/v to 40% v/v for 40 minutes.

Figure 10:
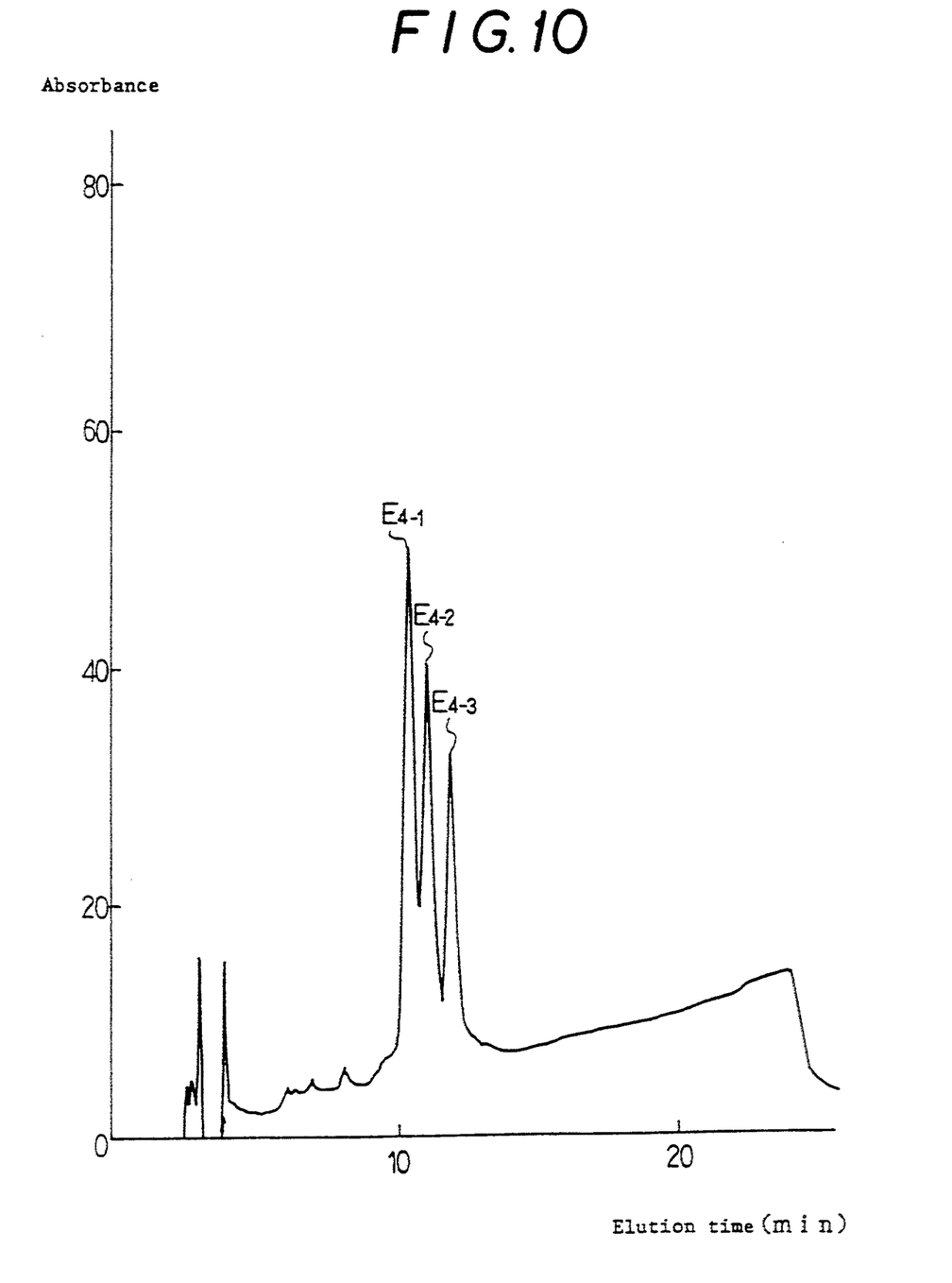
FIG. 10 is an HPLC extraction pattern of the peak E4.

The separated peptide of each peak was collected and then the amino acid composition was analyzed by the same method as the one described in Example 11 to thereby detect cysteic acid. FIG. 10 shows the results.

As a result, cysteic acid was detected from the fraction of the peak E4-1 shown in FIG. 10 (0.41 pmol/pmol). Thus the fraction of the peak E4-1 was further separated by HPLC.

The separation was carried out under the same conditions as those of the above HPLC except that the mobile phase was eluted by linear concentration gradient with acetonitrile of 20% v/v to 30% v/v for 40 minutes.

Figure 11:
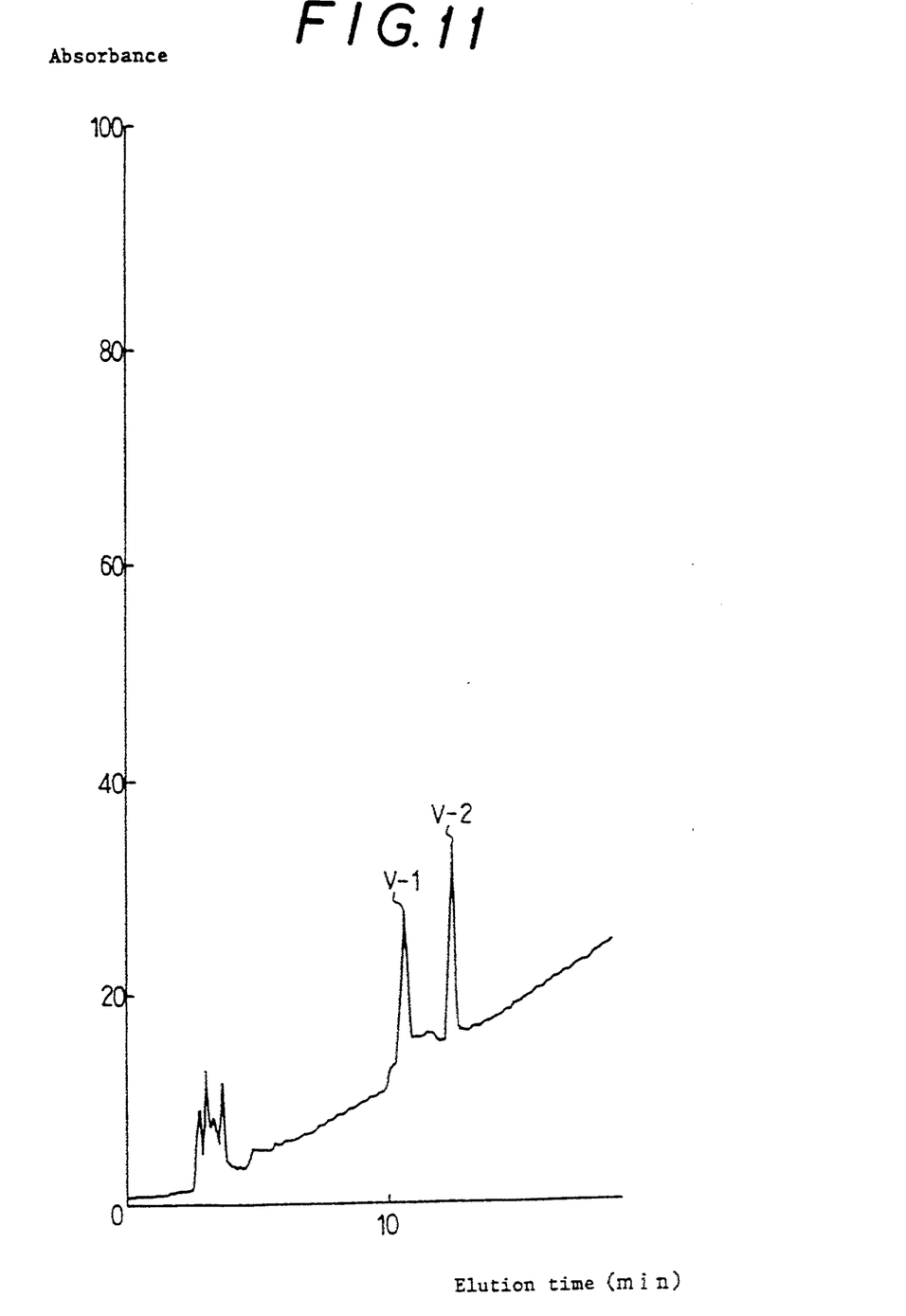
FIG. 11 is an HPLC extraction pattern of the peak E4-1.

As a result, two peptides (peaks) of V-1 and V-2 were obtained as FIG. 11 shows.

The amino acid composition of each peptide was analyzed by the same method as those employed in the above Examples 10 and 11. Table 9 shows the results.

TABLE 9

Amino acid composition of peptide V-1 (unit: mol of each amino acid/mol of peptide)

| Amino acid | Asx | Ser | Gly | Ala | |
|---|---|---|---|---|---|
|  | 2.5(3) | 1.4(1) | 3.6(3) | 1.4(2) | |
|  | Tyr | Lys | Val | Cys* | Trp |
|  | 0.6(1) | 0.5(1) | 1.3(1) | 0.5(1) | ND(1) |

*: results of performic acid oxidation method (Example 11).

Further, the amino acid sequence of the peptide of the fraction V-1 was analyzed. As a result, cystine was found in the 6th cycle and the formation of an interchain disulfide linkage at the 77th cysteine residue of the protein was confirmed. Table 10 shows the results.

TABLE 10

Analysis on amino acid sequence of peptide V-1 (unit: pmol)

| Cycle | 1 | 2 | 3 | 4 | 5 |
|---|---|---|---|---|---|
| Amino acid (pmole) | Val 1537 | Asn 606 | Gly 1850 | Ser 314 | Ala 906 |
| Cycle | 6 | 7 | 8 | 9 | 10 |
| Amino acid (pmole) | Cystine 14 | Trp 156 | Gly 632 | Asp 287 | Asn 337 |
| Cycle | 11 | 12 | 13 | 14 |  |
| Amino acid (pmole) | Gly 534 | Lys 257 | Tyr 186 | Ala 145 |  |

Example 14: Determination of the Position of Interchain Linkage of the 109th Cysteine residues Similar to the above Example 13, the highly pure curculin C obtained in the above Example 4 was digested with an enzyme. Then a digestion fragment containing cystine was taken out of the digestion product to determine the structure. As a result, it was confirmed that the 109th cysteine of the protein formed an interchain disulfide linkage.

The structure of the curculin C thus determined is as follows.

Namely, the 29th cysteine residue and the 52nd cysteine residue form an intrachain disulfide linkage together and both of the 77th cysteine residues and the 109th cysteine residues form interchain disulfide linkages, thus giving a dimer. Further, the curculin C of the present invention has an amino acid sequence as specified in the following sequence list as a monomer.

What is claimed is:

1. Curculin C, having interchain disulfide linkages between the 77th cysteine residues of two monomer chains and between the 109th cysteine residues of said two monomer chains, thus giving a dimer, each said monomer chain having an amino acid sequence as specified in SEQ ID No:i, and each said monomeric chain having an intrachain disulfide linkage between the 29th cysteine residue and the 52nd cysteine residue, said curculin C being obtained by extracting *Curculigo latifolia* fruits or sarcosarp thereof with an aqueous salt solution, thereafter salting out a crude extract from the salt solution and subjecting the resultant precipitate to purification by CM-Sepharose ion exchange chromatography followed by gel filtration chromatography with the use of a Sephadex G-100 column, said curculin C being characterized by a single peak being obtained when said curculin C is separated with the use of a Sephadex G-100 column and 0.01M phosphate buffer solution of pH 6.8, containing 0.5M NaCl.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 114 amino acids (B) TYPE: AMINO ACID
(C) STRANDEDNESS: Not Applicable
(D) TOPOLOGY: linear (ii) MOLECULE TYPE: protein (vi) ORIGINAL SOURCE:
(A) ORGANISM: Curculigo latifolia (xi) SEQUENCE DESCRIPTION: SEQ ID NO:1:

```
Asp Asn Val Leu Leu Ser Gly Gln Thr Leu His Ala Asp His Ser
 1               5                  10                  15

Leu Gln Ala Gly Ala Tyr Thr Leu Thr Ile Gln Asn Lys Cys Asn
                20                  25                  30

Leu Val Lys Tyr Gln Asn Gly Arg Gln Ile Trp Ala Ser Asn Thr
                35                  40                  45

Asp Arg Arg Gly Ser Gly Cys Arg Leu Thr Leu Leu Ser Asp Gly
                50                  55                  60

Asn Leu Val Ile Tyr Asp His Asn Asn Asn Asp Val Asn Gly Ser
                65                  70                  75

Ala Cys Trp Gly Asp Asn Gly Lys Tyr Ala Leu Val Leu Gln Lys
                80                  85                  90

Asp Gly Arg Phe Val Ile Tyr Gly Pro Val Leu Trp Ser Leu Gly
                95                  100                 105

Pro Asn Gly Cys Arg Arg Val Asn Gly
                110
```